United States Patent [19]

Burlamacchi et al.

[11] 4,013,978
[45] Mar. 22, 1977

[54] LASERS AND PHOTOCOAGULATORS

[75] Inventors: Pio Burlamacchi; Riccardo Pratesi; Umberto Vanni, all of Florence, Italy

[73] Assignee: Consiglio Nazionale delle Richerche, Rome, Italy

[22] Filed: Sept. 25, 1975

[21] Appl. No.: 616,889

[30] Foreign Application Priority Data

Sept. 27, 1974 Italy .................................. 9577/74

[52] U.S. Cl. ....................... 331/94.5 L; 331/94.5 P
[51] Int. Cl.² ......................................... H01S 3/092
[58] Field of Search .................................. 331/94.5

[56] References Cited
UNITED STATES PATENTS

| 3,720,213 | 3/1973 | Hobart et al. | 331/DIG. 1 |
| 3,890,578 | 6/1975 | Wang | 331/94.5 L |
| 3,913,033 | 10/1975 | Tuccio | 331/94.5 L |
| 3,931,594 | 1/1976 | Schafer | 331/94.5 L |

Primary Examiner—William L. Sikes

[57] ABSTRACT

A photocoagulator is described incorporating a selected light source. The selected light source is a waveguide laser of the type using an active liquid comprising a dye in solution.

The laser is so constructed that a cell containing the active liquid and a reservoir, rigid with the cell, for replenishing the liquid in the cell, form a single unit which can be readily removed from the remainder of the laser. An optical pumping source which forms part of the remainder of the laser is arranged to set up a heat gradient in the cell which tends to collimate the stimulated emission in the cell thus avoiding the need for accurate alignment of the reflectors at opposite ends of the cell.

9 Claims, 5 Drawing Figures

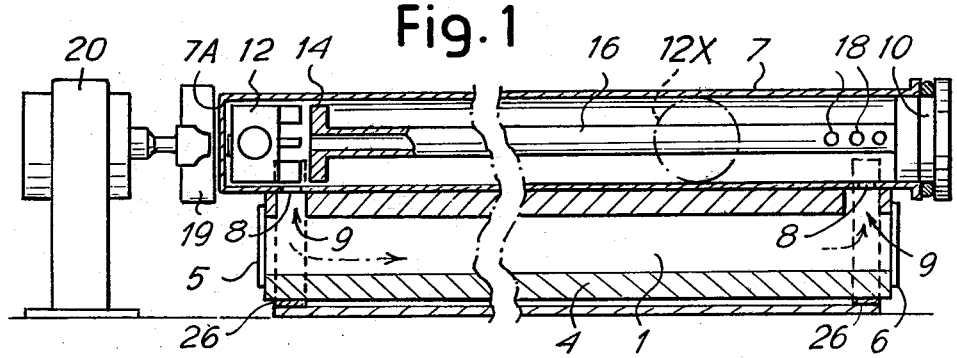
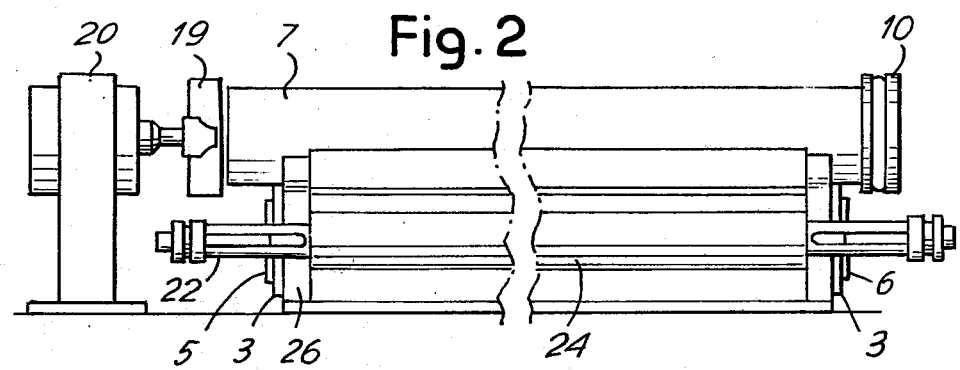
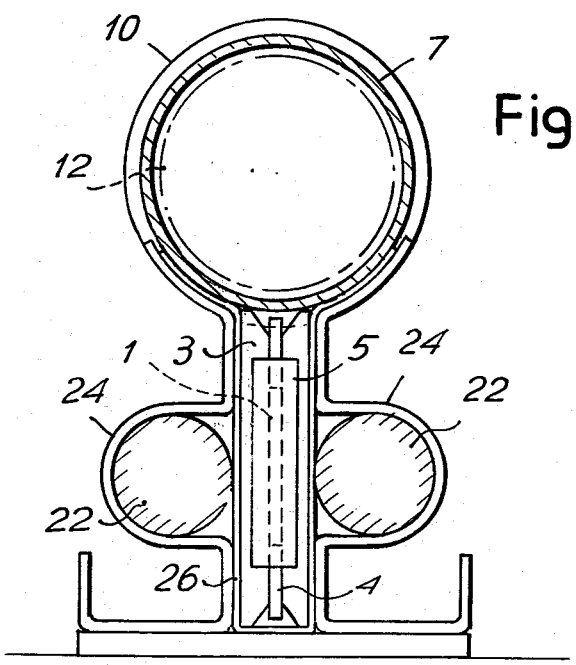

LASERS AND PHOTOCOAGULATORS

BACKGROUND OF THE INVENTION

1. Field of the Invention

The present invention relates to lasers, for use with photo-coagulators, for example.

2. Description of the Prior Art

Lasers have been used in photocoagulators to enable photocoagulation therapy to be used in the treatment of various eye disorders.

Such lasers have been complex and involved a high degree of precision and consequently these have proved very expensive. Furthermore these lasers cannot be readily converted to operate at a different wavelength, and if a fault develops skilled personnel are required to rectify the fault.

It is an object of the invention to provide a laser for a photocoagulator which is easy and cheap to construct, which can be readily converted to operate at different wavelengths, and which can be readily maintained.

SUMMARY OF THE INVENTION

According to the present invention there is provided a photocoagulator for opthalmic applications in which the energy source of the photocoagulator is formed by a wave guide laser in which the active liquid comprises a dye in solution.

According to the present invention there is further provided a wave guide laser comprising a housing supporting a pair of flash tubes on opposite sides of a cell receiving recess and also supporting reflectors for said flash tubes, an elongate wave guide cell removably locatable in the recess, the cell having two opposite parallel transparent walls, each of which is arranged to face a corresponding flash tube when the cell is located in the recess. a reservoir communication with opposite longitudinal ends of the cell, the cell and the reservoir containing an active liquid comprising a dye in solution and circulation means for circulating the liquid between the cell and the reservoir.

According to the present invention there is still further provided a laser comprising an elongate cell and an elongate reservoir lying side by side and rigidly secured to one another along adjacent walls, the cell and the reservoir containing a solution of an active dye and being in communication with one another at adjacent longitudinal end portions, circulating means located within the reservoir operable to circulate the dye solution around the loop formed by the cell and reservoir, at least one of the walls of the cell which does not face the reservoir being translucent, a housing arranged to locate and support the cell and the reservoir, and from which the cell and reservoir can be readily removed, and light source means mounted on the housing and operable when the cell is located on the housing to inject light through the translucent wall of the cell into the solution of active dye to stimulate emission of radiation, one of the opposite longitudinal end walls of the cell being reflective and the other being only partially reflective and defining the output of the laser.

BRIEF DESCRIPTION OF THE DRAWINGS

A waveguide dye laser embodying the invention will now be described, by way of example with reference to the accompanying diagrammatic drawings in which:

FIG. 1 is a longitudinal section through the laser;

FIG. 2 is a front elevation of the laser of FIG. 1;

FIG. 3 is an end elevation of the laser of FIG. 1; and

DESCRIPTION OF THE PREFERRED EMBODIMENT

Figure 4:
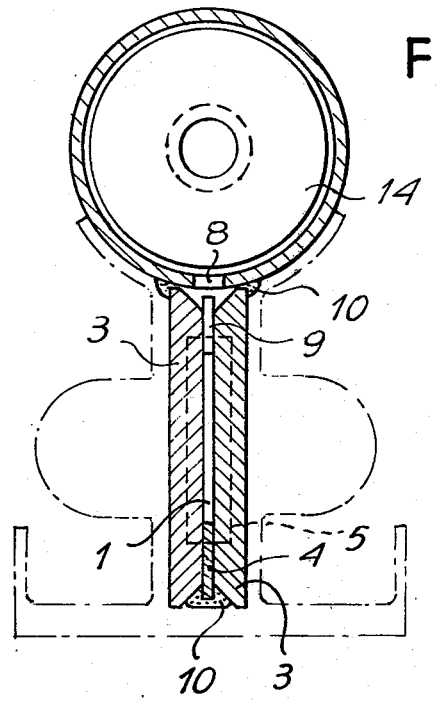
FIGS. 4 and 5 are different cross-section through the laser of FIG. 1.
Figure 5:
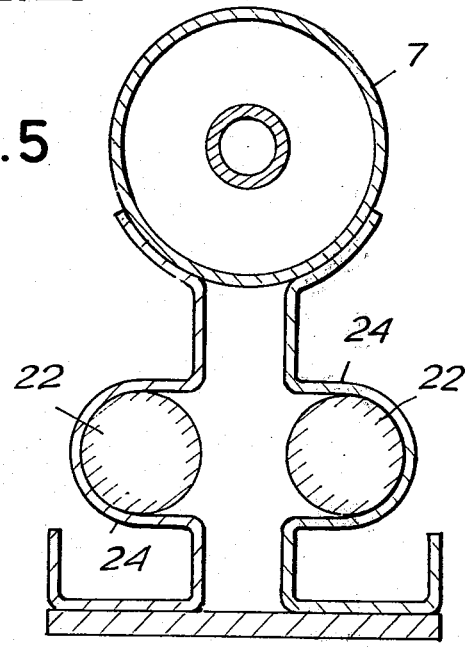

Lasers have been used as a light source which, when focussed on the human eye retina, effect the coagulation thereof. Photocoagulation therapy is advantageously used for ablatio retinae treatment, treatments of tumours, diabetic retinitis, and the like.

A pulse duration of from 1 to 5 $\mu$s appears to be the most suitable to minimize the radiant energy required for the photocoagulation. The laser to be described is particularly suitable for the above applications but is of course not limited to these applications.

As shown in FIG. 1 the laser includes an elongate cell 1 of rectangular cross-section defined by two parallel elongate glass sheets 3 which are spaced from one another at their longitudinal edges by two elongate separators 4. The cell is filled with an active material in an organic solvent, the active material being a dye. The spacing between the sheets 3 is advantageously 0.5 mm when the active material filling the cell is rhodamine 6G. Also the length of the cell is advantageously from 70 to 150 mm, and the height of the cell is advantageously from 8 to 10 mm. The cell is closed at one longitudinal end by a polished stainless steel sheet 3 and on the other longitudinal end by a part silvered mirror 6 which forms the outlet window. The sheets 3 advantageously have a thickness of 2 mm; the separators 4, are advantageously of glass or of stainless steel, and are polished on their faces which are the internal surfaces of the cell. A stainless steel cylindrical tank 7 extending parallel to the cell is mounted directly on top of the cell. The tank 7 communicates with the cell directly through two holes 8 in the wall of the tank, which are aligned with corresponding ones of two gaps 9 in the upper of the two separators 4. The points of communication are located adjacent opposite ends of the cell. The tank 7, which forms a reservoir for a dye solution is adhesively secured to the two sheets with glue 10, which also seals together the two sheets 3. The capacity of the reservoir is advantageously at few cubic centimeters since the capacity of the cell is approximately 20–50 cubic millimeters. The dye solution in reservoir and cell are slowly circulated around the loop formed by the cell and tank to produce gradual dye solution change in the cell and to equalise the temperature difference between the solution in the cell and in the tank. The tank 7 has one closed longitudinal end 7A and an opening at its other longitudinal end which is closed by a plug 10 and a packing. The rotor of a centrifugal pump 12 is housed inside of the tank adjacent the closed end 7A, and when operative pumps the liquid in the tank to the cell 1 at a speed of about 5 centimeters/second. The rotor is carried by a baffle 14 which is secured to a hollow rod 16 projecting from the plug 10. The hollow rod has three holes in a portion of the circumferential surface of the rod that lies adjacent the plug. The rotor 12 magnetically cooperates with a magnet 19 through the end wall 7A of the tank. The magnet 19 is coupled for rotation to a small electric motor 20 (0.1 watt). In operation when the motor 20 is energised the magnet 19 rotates and in turn causes the rotor 12 to rotate. Rotation of the rotor draws liquid through the hollow tube 16 and pumps it into the cell 1, as indicated by the arrows. The pump formed by the rotor 12, the magnet 19 and the motor 20 can be replaced by a movable metal ball housed in the cylinder 7, when the laser is used in an application where it is being constantly moved, for example when used in association with an opthalmoscope. The stainless steel sheet 5 closing one end of the cell 1 forms mirror at that end of the cell and glass sheet 6 at the other end of the cell has relatively low reflectivity so as to enable a laser beam to escape from the cell. Two flash tubes 22, each partially surrounded by a corresponding reflector 24 made of polished aluminium, flank the cell 1 and are energisable to optically "pump" the cell, that is to stimulate emission of radiation in the active material in the cell.

The cell 1, the reserve tank and the rotor 12 thus form a single unit which can be readily removed for replacement or inspection. Supports 26 are provided to support and locate the removable unit.

The flash tubes are energised from the discharge of a capacitor (approx. 0.1 $\mu$ F) which is normally charged to the voltage level of from 6 to 10 Kv. The active material, because of the refractive index gradients produced in the cell due to heat irradiated by the flash tubes, becomes "self-guiding" and the whole cell becomes a closed resonator. In particular it will be appreciated that the energy output from the cell does not depend upon the precise alignment of the mirrors in the cell or upon the precise temperature of the laser while operating; factors which are critical in more conventional lasers. The wavelength of the light output from the laser can be varied over the range of the visible spectrum by using different dyes as the active material in the cell. Even without changing the type of dye used the wavelength of the light output can be varied over the fluorescence band of each dye, by varying its concentration. In general the emission takes place on several very narrow lines, within a band ranging from 15 to 20 A.

The light emission from the laser can be directly coupled to an opthalmoscope. The opthalmoscope incorporates a variable focal length lens which can be operated to reduce the size of the output beam from the laser and to direct the reduced beam on the retina of a patient. The outlet surface of the cell has dimensions of 0.5 × 8 mm, and can be appropriately diaphragmed. The output beam from the cell is made visible on the retina by an appropriate lighting. This constitutes a positive sighting system, in that the area to be photocoagulated can be observed upon laser ignition.

As the energy required for the retina coagulation varies from person to person, and depends upon the dimensions of the zone to be treated, the power of the laser must be variable.

The wave guide laser described is thus a particularly suitable source for a photocoagulator, since it is easily replaceable, compact in structure, and constructed with a dye reservoir and wave guide mirrors, which are independent of the optical pumping system. The entire laser source is thus formed only by two independent sections. The first section is formed by the lamp 22 with its own supports, by the reflectors 24 which also form the cell support, and by the electric motor 20. The second section is formed by the reserve tank 7 and the wave guide cell 1. The two sections are readily separable so that in a simple operation (which may be effected by non-specialist staff) the second section can be replaced by one filled with a different dye when it is desired to change the wave length of the emitted light (green, yellow or red, for example) or merely replaced when the existing section becomes damaged or polluted.

The wave guide dye laser described has the following features:
1. it operates at a relatively low voltage, consequently extending the life of the flash tubes and reducing insulation problems;
2. it provides repeatable results and is safe in operation;
3. it does not require a rapid circulation of the active liquid, but only a gradual change, thus enabling the laser to be relatively compact;
4. it does not require a strict alignment of the mirrors;
5. apart from the flash tubes, the laser does not require a sophisticated structural and/or assembling technology.

Alternatively, the circulation means may comprise a member 12X, especially in the form of a ball, as shown in chain in FIG. 1, which is movable within the reservoir 7.

We claim:
1. A wave guide laser comprising
   a resonant cavity;
   a housing defining a cell receiving recess;
   a pair of flash tubes supported by the housing on opposite sides of the cell receiving recess;
   reflectors for said flash tubes supported by the housing;
   an elongate wave guide cell removably located in the recess, the cell having two opposite parallel transparent walls, each of which is arranged to face a corresponding flash tube when the cell is located in the recess;
   a reservoir secured to the cell and communicating with opposite longitudinal ends of the cell;
   an active liquid comprising a dye in solution filling the cell and the reservoir; and
   circulation means located in the liquid for circulating the liquid between the cell and the reservoir.
2. A laser according to claim 1, wherein the cell includes
   a reflective member closing one longitudinal end of the cell, and
   a partially reflective member closing the other longitudinal end of the cell, the partially reflective member also forming a light outlet for the laser beam when produced.
3. A laser according to claim 1 wherein the reservoir has openings at its opposite end portions and the cell has openings at its opposite end portions, corresponding openings in the reservoir and the cell being aligned to form the said communication between the reservoir and the cell, and including an adhesive securing the cell and reservoir together around the aligned openings.
4. A laser according to claim 1 wherein the reservoir comprises a hollow cylindrical member and wherein the housing includes support brackets for supporting the hollow cylindrical member.
5. A laser according to claim 1, wherein the circulation means includes a rotor located within the reservoir and magnetically coupled to a rotary member mounted on the housing whereby rotation of the rotary member causes rotation of the rotor.
6. A laser according to claim 1, wherein the circulation means comprises a member located in the reser- voir and movable to displace liquid in the reservoir in response to a change in attitude of the reservoir.

7. A laser according to claim 6 wherein said member is spherical.

8. A laser comprising a resonant cavity an elongate cell an elongate reservoir, the cell and the reservoir lying side by side, means rigidly securing the cell and the reservoir along adjacent walls and providing communication between the cell and reservoir at adjacent longitudinal end portions, a solution of an active dye filling the cell and the reservoir, circulating means located within the reservoir and operable to circulate the dye solution around the loop formed by the cell and reservoir, the cell having four side walls and two longitudinal end walls with at least one of its side walls which does not face the reservoir being translucent, one of its opposite longitudinal end walls being reflective, and its other end wall being only partially reflective to define the output of the laser, a housing arranged to locate and support the cell and the reservoir, and from which the cell and reservoir can be readily removed, and light source means mounted on the housing operable when the cell is located on the housing to inject light through the translucent wall of the cell into the solution of active dye to stimulate emission of radiation.

9. A laser according to claim 8 including a prime mover mounted on the housing and operable to generate a varying magnetic field through the walls of the reservoir to drive the circulating means.

* * * * *